(12) United States Patent
Myers

(10) Patent No.: US 7,182,239 B1
(45) Date of Patent: Feb. 27, 2007

(54) SEGMENTED INTRODUCER DEVICE FOR A CIRCULAR SURGICAL STAPLER

(76) Inventor: Stephan R. Myers, 510 Cedarwood Dr., Lexington, OH (US) 44904

( * ) Notice: Subject to any disclaimer, the term of this patent is extended or adjusted under 35 U.S.C. 154(b) by 0 days.

(21) Appl. No.: 11/212,377

(22) Filed: Aug. 26, 2005

Related U.S. Application Data

(60) Provisional application No. 60/604,946, filed on Aug. 27, 2004.

(51) Int. Cl.
*A61B 17/068* (2006.01)

(52) U.S. Cl. ............... 227/175.1; 227/19; 606/139; 606/148; 606/151; 606/153

(58) Field of Classification Search .............. 227/19, 227/175.1, 176.1, 178.1, 179.1, 180.1; 606/151, 606/139, 148, 153, 191, 219
See application file for complete search history.

(56) References Cited

U.S. PATENT DOCUMENTS

| | | | | |
|---|---|---|---|---|
| 4,505,272 A | * | 3/1985 | Utyamyshev et al. | 227/179.1 |
| 4,700,703 A | * | 10/1987 | Resnick et al. | 227/176.1 |
| 4,817,847 A | | 4/1989 | Redtenbacher et al. | 227/19 |
| 5,104,025 A | * | 4/1992 | Main et al. | 227/175.1 |
| 5,197,649 A | * | 3/1993 | Bessler et al. | 227/179.1 |
| 5,205,459 A | | 4/1993 | Brinkerhoff et al. | 227/179 |
| 5,222,963 A | * | 6/1993 | Brinkerhoff et al. | 606/153 |
| 5,275,322 A | | 1/1994 | Brinkerhoff et al. | 227/175 |
| 5,309,927 A | * | 5/1994 | Welch | 128/898 |
| 5,314,436 A | | 5/1994 | Wilk | 606/153 |
| 5,355,897 A | | 10/1994 | Pietrafitta et al. | 128/898 |
| 5,404,870 A | | 4/1995 | Brinkerhoff et al. | 128/3 |
| 5,445,644 A | | 8/1995 | Pietrafitta et al. | 606/151 |
| 5,669,918 A | | 9/1997 | Balazs et al. | 606/139 |
| 5,836,503 A | | 11/1998 | Ehrenfels et al. | 227/175.1 |
| 6,945,444 B2 | * | 9/2005 | Gresham et al. | 227/175.1 |
| 6,957,758 B2 | * | 10/2005 | Aranyi | 227/176.1 |
| 6,959,851 B2 | * | 11/2005 | Heinrich | 227/175.1 |
| 6,981,979 B2 | * | 1/2006 | NIcolo | 606/153 |

* cited by examiner

*Primary Examiner*—Scott A. Smith
(74) *Attorney, Agent, or Firm*—Renner, Kenner, Greive, Bobak, Taylor & Weber

(57) ABSTRACT

A segmented introducer device is capable of fitting onto the center rods of circular stapling devices having different stapler head diameters. Multiple body segments are provided depending upon the needs for a given surgical stapler, and the body segments are selectively fit together to provide rod through apertures and a rod bore to receive the center rod of the surgical stapler. The introducer preferably includes blades to help spread tissue as the introducer device is advanced to the tissue site on the head of the stapler. A retraction wire is provided at the tip of the introducer device to aid in its retrieval from a tissue site.

6 Claims, 12 Drawing Sheets

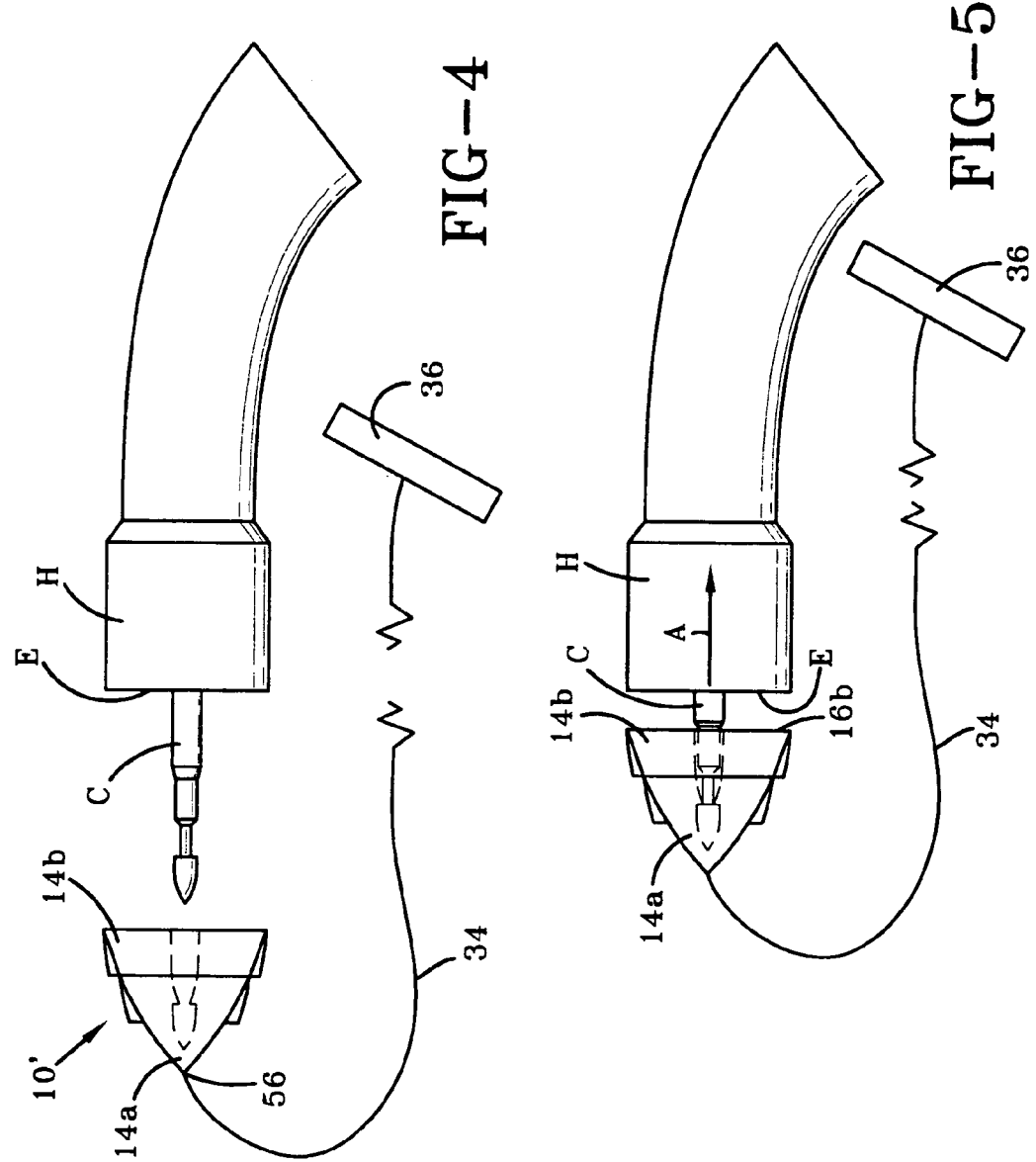

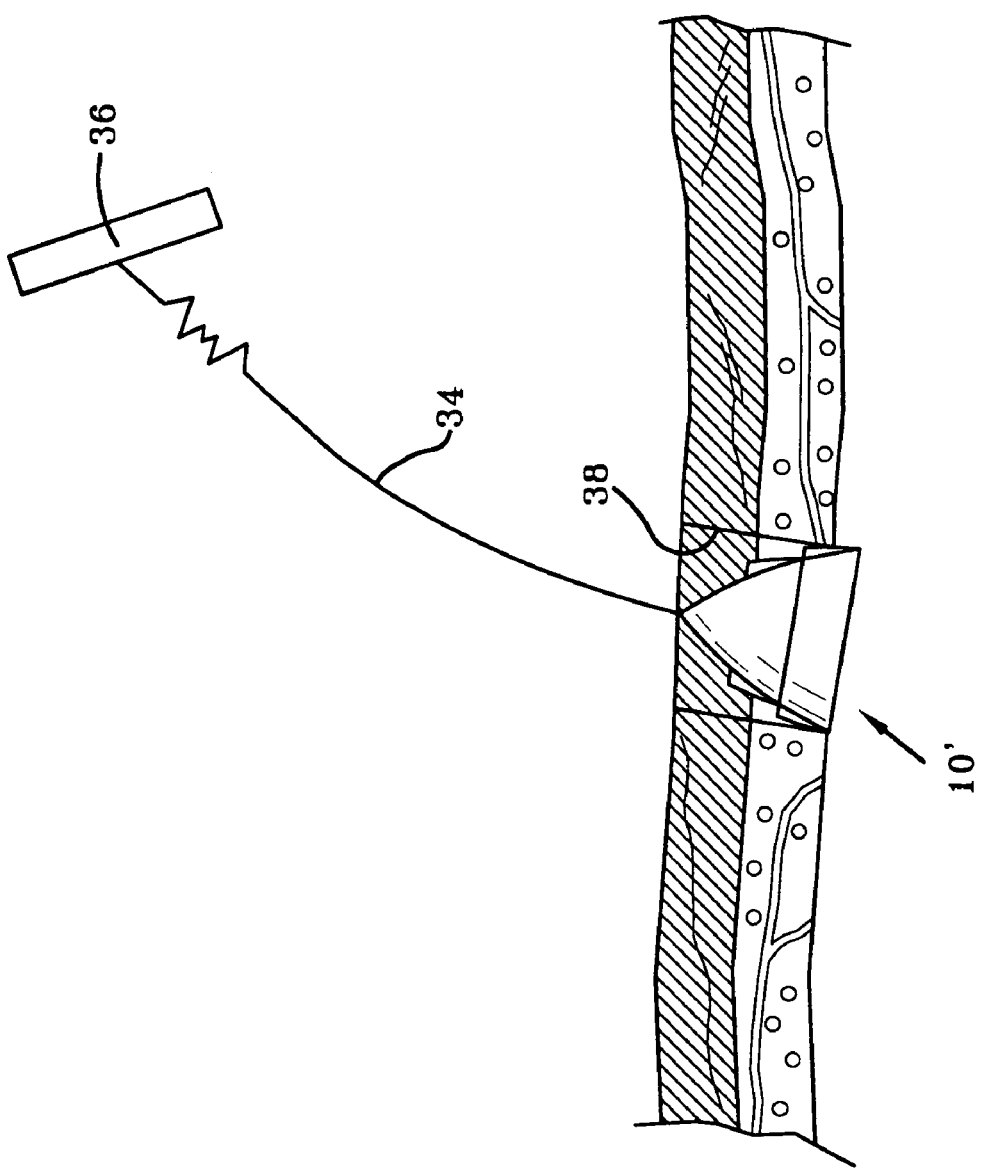

US 7,182,239 B1

SEGMENTED INTRODUCER DEVICE FOR A CIRCULAR SURGICAL STAPLER

RELATED PATENT APPLICATIONS

This application is a non provisional application claiming the priority filing date of U.S. Provisional Patent Application No. 60/604,946, filed Aug. 27, 2004, incorporated herein by reference.

BACKGROUND OF THE INVENTION

The use of circular surgical staplers for end-to-end, end-to-side, and side-to-side anastomoses, and for others uses in vivo, is well known. A particular example of such a stapler includes the stapler described in U.S. Pat. No. 5,104,025, entitled "Intraluminal Anastomotic Surgical Stapler with Detached Anvil," wherein an anvil assembly is mounted on the end of a pointed center rod to be manipulated relative to a staple assembly on the end of a tubular housing of the instrument, in order to drive staples through the desired tissue, against the anvil backing, to create the desired connection. The pointed center rod is retractable into the head of the surgical stapler, such that it may be hidden during insertion of the stapler head to the target tissue site. Recently, surgical staplers have been employed in laparoscopic operations by passing the stapler through a small incision in the abdominal wall. However, the head is shaped such that it is difficult to unintrusively advance the head through the abdominal tissue to the target tissue site, and the prior art has provided tapered introducers to fit onto the center rod to provide the head with a tapered insertion end to aid in such introduction.

The present invention addresses what is seen to be failures of the prior art in such tapered introducer designs, and an improved introducer is provided.

SUMMARY OF THE INVENTION

The present invention provides a segmented introducer device that is capable of fitting onto the center rods of surgical stapling devices having different stapler head diameters at their insertion ends. For example, the present invention is particularly adapted to interact with surgical staplers such as the ENDOPATH ILS and PROXIMATE ILS staplers produced by Ethicon Endo-Surgery, Inc. In the present embodiment, there are four body segments, although the present invention is not to be limited thereto or thereby, it being understood that more or less body segments might be practiced in accordance with this invention, depending upon the needs for a given surgical stapler and stapler head. The body segments fit together through a snap fit, and three provide through apertures while one provides a center rod bore to receive the center rod of a surgical stapler. The first body segment is generally conical, providing an insertion tip and also providing the aforementioned center rod bore. Each body segment joins smoothly with one or more neighboring body segments to create a smooth, rounded exterior surface surround the center rod of a surgical stapler when receive thereon. Each body segment has an increased diameter at a bottom edge, and these diameters are intended to match the diameters of various insertion ends of the stapler heads of various surgical staplers. Thus, depending upon the diameter of the stapler head of the particular surgical stapler being employed, a different number of body segments might be employed, as appropriate to create an insertion device on the surgical stapler having an insertion tip and a smooth rounded exterior surface running from the insertion tip to abut the insertion end. In particular embodiments, each body segment includes blades that help spread tissue as the tapered introducer on the head of the stapler device is advanced to the target site.

This invention provides an introducer device adapted for use with a plurality of surgical staplers, wherein each of the plurality of surgical staplers include a stapler head having an insertion end of circular cross section, a center rod having a tapered head and adapted to be selectively extendable beyond the insertion end of the stapler head and selectively retractable into the stapler head, each stapler head of each of the plurality of surgical staplers having a different diameter. The introducer device includes a first body segment having an insertion end opposite a base end, a sidewall tapering from said base end to said insertion end to define an insertion tip, a center rod bore extending from an open end thereof at said base end toward said insertion tip and having a head grip portion adapted to selectively engage the tapered head of the center rod of any of the plurality of surgical staplers to secure said first body segment to cover said tapered head of said center rod, and a female connection bore extending from an open end thereof at said base end toward said insertion end. The device further includes a second body segment having an insertion end opposite a base end, a sidewall tapering from said base end to said insertion end, a through aperture adapted to received the center rod of any of the plurality of surgical staplers, and a male connection member extending from said insertion end to selectively engage said female connection bore of said first body segment, wherein said base end of said first body segment has a base end diameter substantially equal to the diameter of the insertion end of the stapler head of one of the plurality of surgical staplers and said base end of said second body segment has a base end diameter substantially equal to the diameter of the insertion end of the stapler head of another of the plurality of surgical staplers, said base end diameter of said first body segment being smaller than said base end diameter of said second body segment.

Preferably, the insertion end of said second body segment has an insertion end diameter that is substantially equal to base end diameter of said base end of said first body segment.

BRIEF DESCRIPTION OF THE DRAWINGS

FIG. 4 shows a two-segment introducer device as in FIGS. 1–3 joined together and being aligned with the center post on a surgical stapler;

FIG. 5 shows the introducer device of FIG. 4 after being secured to the center rod;

FIG. 13 shows the removal of the introducer device with the retraction wire.

PREFERRED EMBODIMENT OF THE INVENTION

Figure 1:
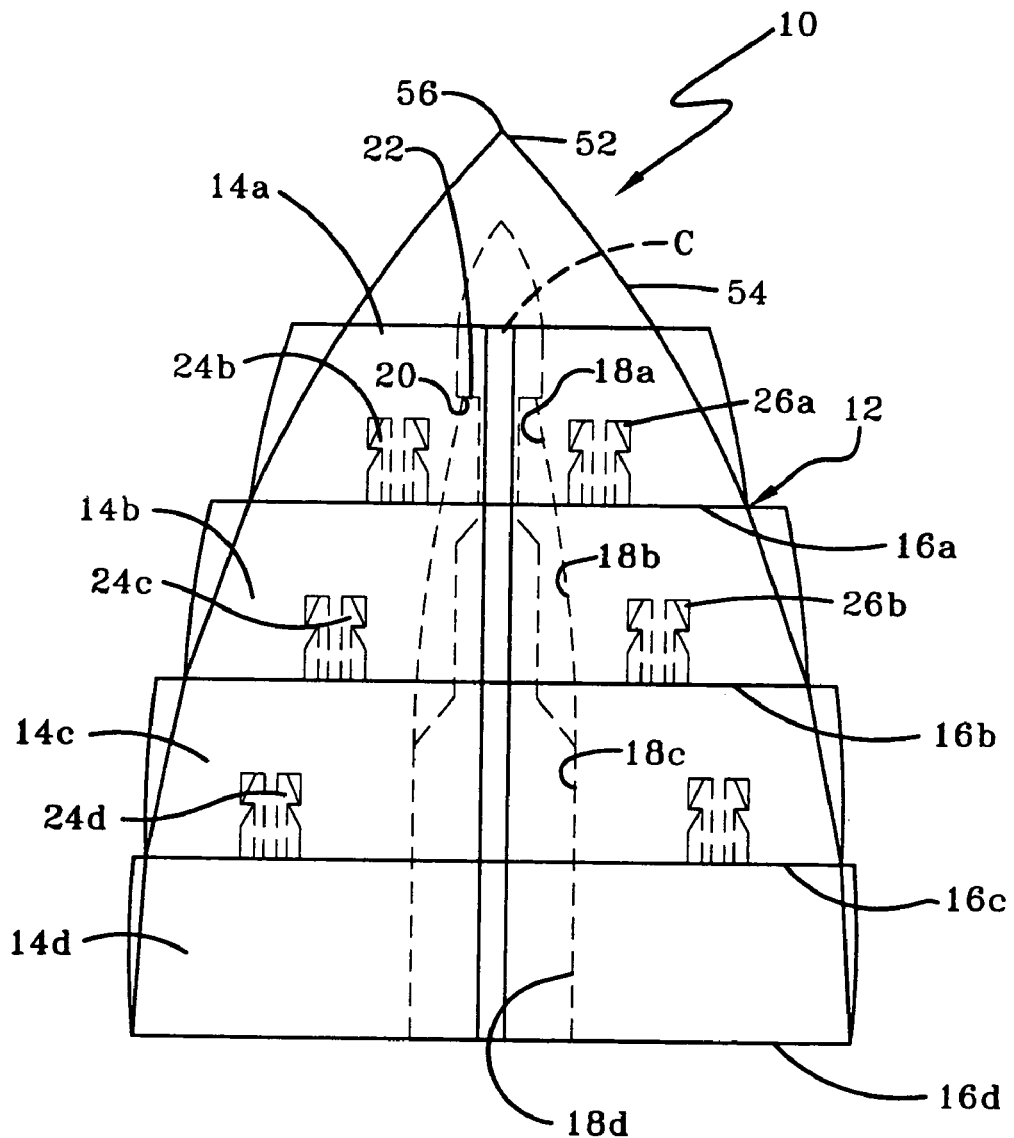
FIG. 1 is a side elevational view of the introducer device according to this invention, shown with four body segments.
Figure 2:
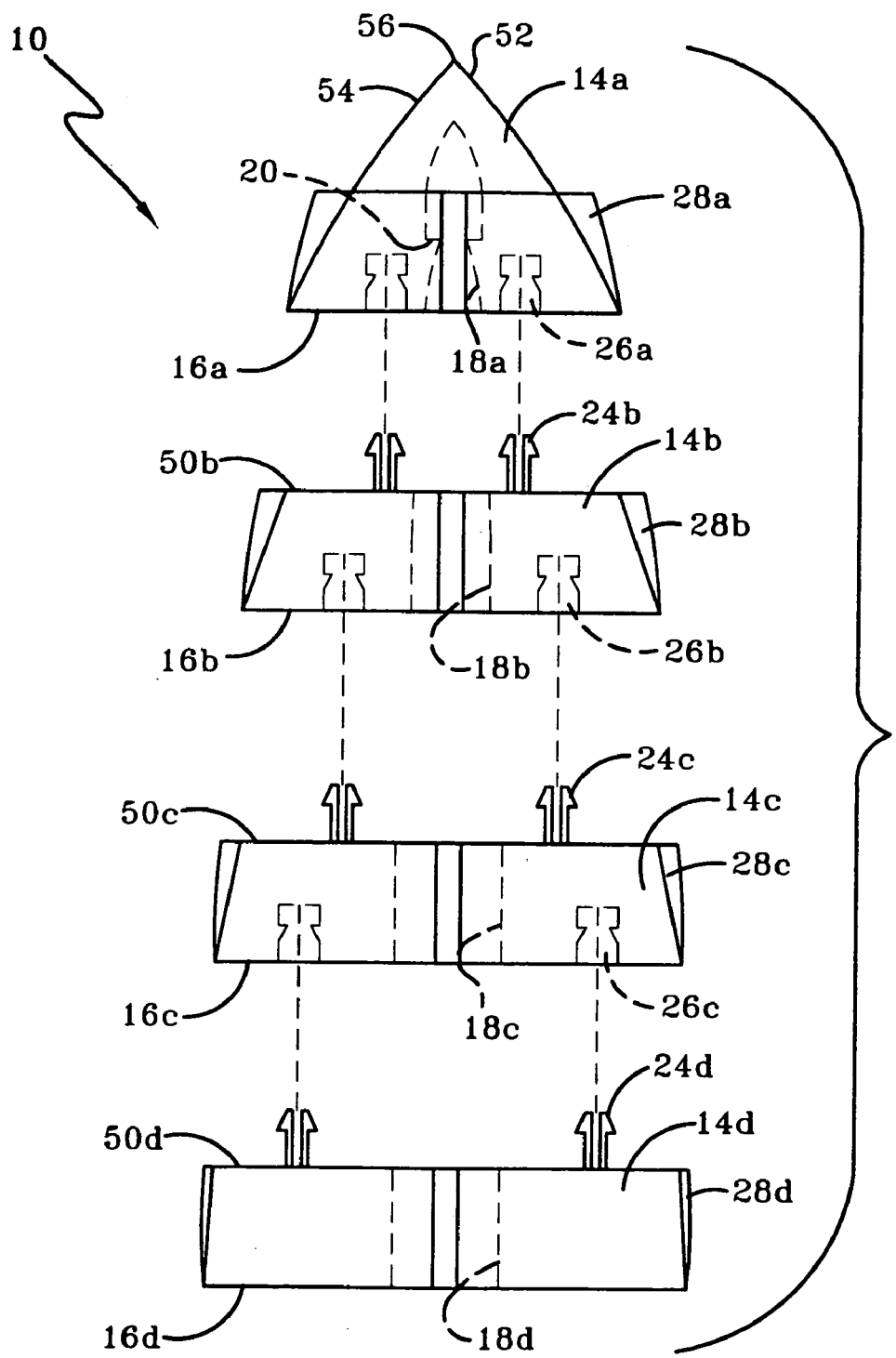
FIG. 2 shows the introducer device of FIG. 1 with each body segment separated from its mating body segment or segments.
Figure 3:
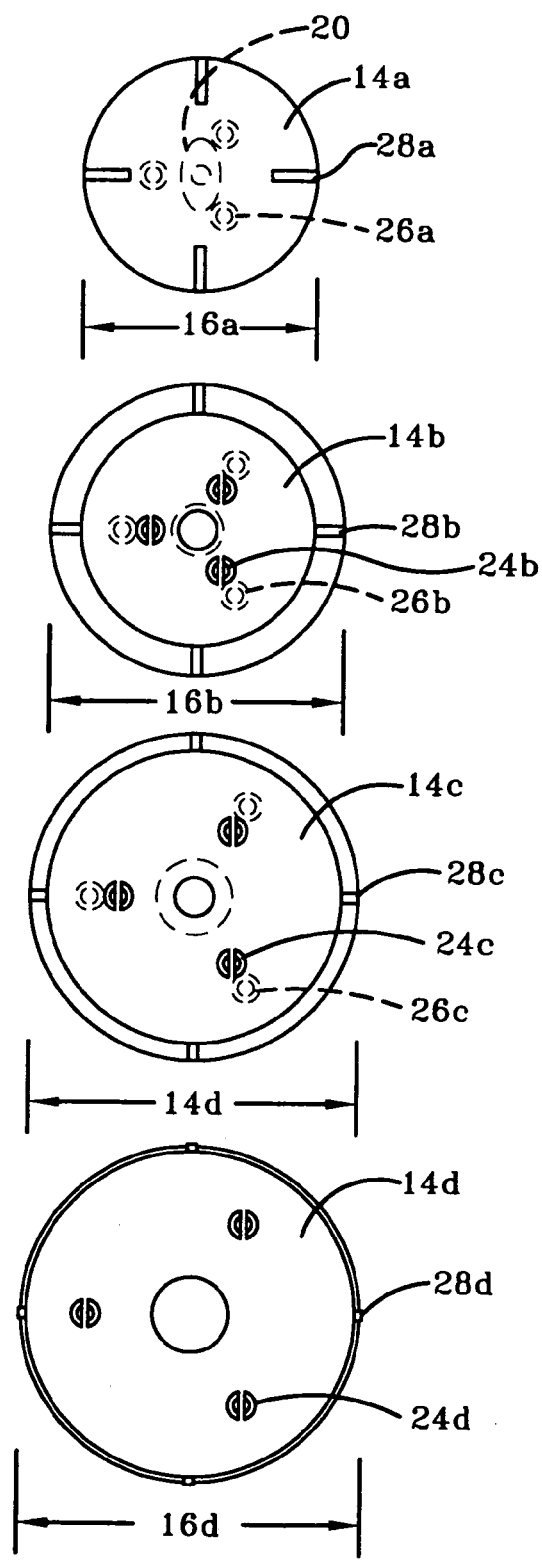
FIG. 3 is a top plan view of the individual body segments of FIG. 2.

With reference to FIGS. 1–3, it can be seen that an introducer device according to this invention is designated generally by the numeral 10. Introducer device 10 includes a body portion 12 that, in this preferred embodiment, is selectively provided with one or more body segments 14a, 14b, 14c, 14d. Four body segments (14a–d) have been provided in this embodiment, but the present invention is not limited thereto or thereby. The four body segments are generally circular in cross-section (FIG. 3) and have base ends 16a, 16b, 16c, 16d that are specifically sized to allow the introducer device 10 to be selectively employed with surgical staplers having different sized stapler head diameters. More particularly, base end 16a has a diameter selected to match the diameter at the insertion end of one stapler head of a surgical stapler, base end 16b has a larger diameter selected to match the diameter at the insertion end of a different size stapler head, and base end 16c and 16d have successively larger diameters for the same reason. It should also be appreciated that each body segment 14b–c has an insertion end (designated by 50b, 50c, and 50d) of a diameter substantially equal to the base end of the body segment above it, and this allows them to be fit together to create a smooth exterior surface even at the areas at which they join together. Preferably, first body segment 14a includes an insertion end 52, and sidewall 54 is tapered from base wall 16a to insertion end 52 to define an insertion tip 56.

The bottom three body segments 14b, 14c, 14d each provide through apertures 18.b, 18c, 18d, respectively, for allowing for the passage of a center rod C (in phantom, FIG. 1) of a surgical stapler. Top most body segment 14a provides a center rod bore 18a that has a head grip portion 20 that interacts with the tapered head of the center rod C to hold the center rod C inserted in top body segment 14a. More particularly, head grip portion 20, or at least the portion of top body segment 14a proximate head grip portion 20 and bore 18a, is formed of a resilient material that gives to pressure as center rod C is inserted therein, and, once fully inserted, head grip portion 20 interacts with the flat portions 22 of center rod C to hold center rod C in place.

It is known that surgical staplers are available with stapler heads of different diameters. If a stapler head has an insertion end diameter substantially equal to the diameter at base end 16a of body segment 14a, it is only necessary to employ body segment 14a as the introducer device. However, as the stapler head diameter gets larger, more body segments are employed, and the body segments are specifically produced to have base diameters corresponding with the diameters of available stapler heads. In order to join the individual body segments 14a–d, the bottom three body segments 14b–d include male connection members 24b, 24c, 24d, respectively, which mate with female connection bores 26a, 26b, 26c provided on respective upper neighboring body segments. That is, male connection members 24b mate with peg bores 26a on body segment 14a, snap 24c mate with peg bores 26b on body segment 14b, and male connection members 24d mate with peg bores 26c on body segment 14c. Again, the number of body segments 14a–14d that are employed will depend upon the diameter of the stapling head to which the introducer device 10 is to be fitted. Each body segment 14a–d includes blades 28a–d, respectively to aid in the insertion of the introducer device through tissue, muscle, etc. Blades 28a–d are preferably symmetrically spaced about the circumference of their respective body segments 14a–d. In the embodiment of FIGS. 1–3, four blades are provided on each body segment, at every 90 degrees around the circumference. This is preferred. An alternative is shown in FIGS. 4–13, wherein only two blades are employed.

Referring now to FIG. 4, the attachment of a two-segment introducer device 10' with a surgical stapler as having a stapler head H and center post C is shown by way of example. It will be appreciated how single, triple, and quadruple or more segmented introducer devices may be employed.

Figure 6:
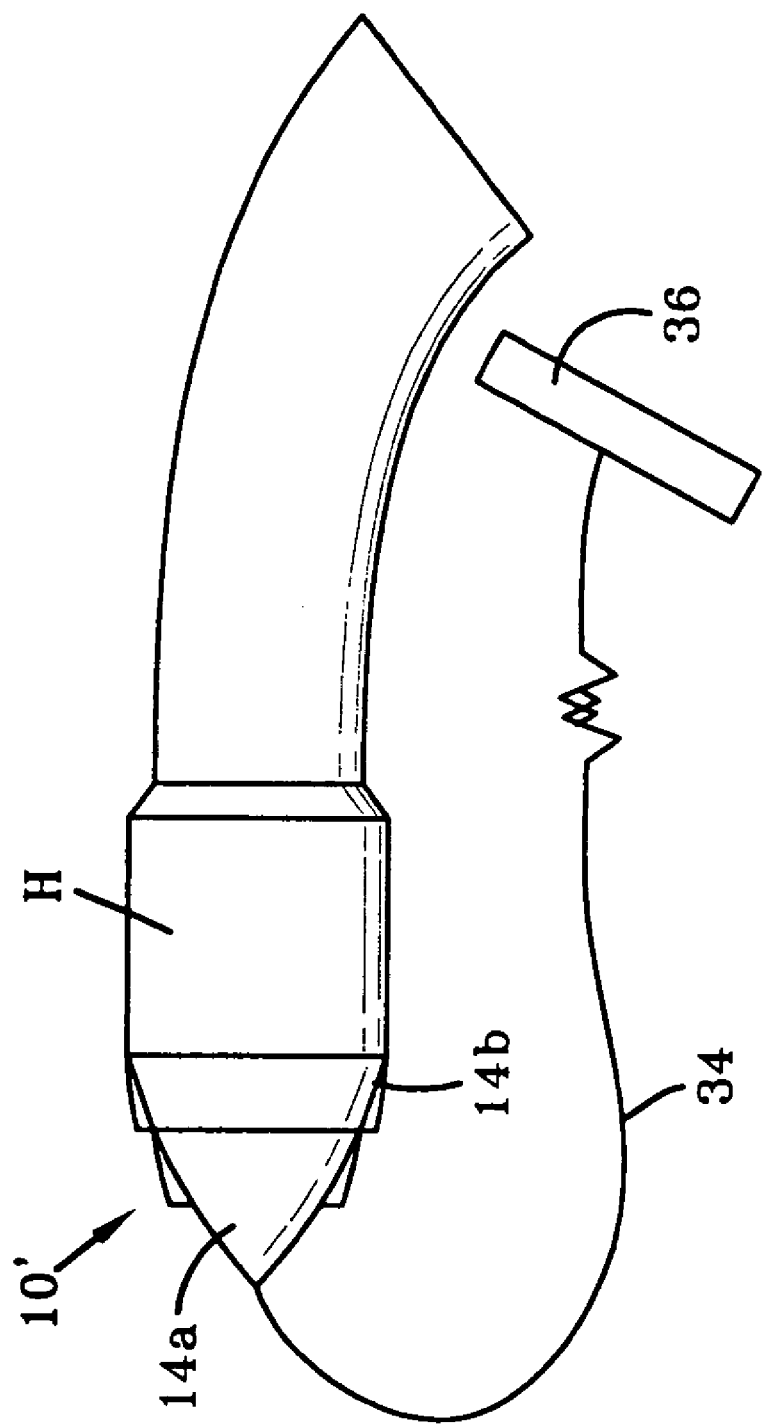
FIG. 6 shows the introducer device of FIGS. 4 and 5 after being fixed to the center rod and after retracting the center rod to mate the introducer device flush with the stapler head.

In FIG. 4, body segments 14a and 14b have been connected, and a further aspect of this invention is shown in that body segment 14a at tip 32, includes an attached retraction wire 34 and grip 36. In FIGS. 5 and 6, it can be seen that this introducer device 10' is fitted onto center post C, as already described, and, as generally know, center post C is retracted in the direction of arrow A until introducer device 10', at diameter 16b of body segment 14b is flush with the diameter of the lead portion of head H.

Figure 7:
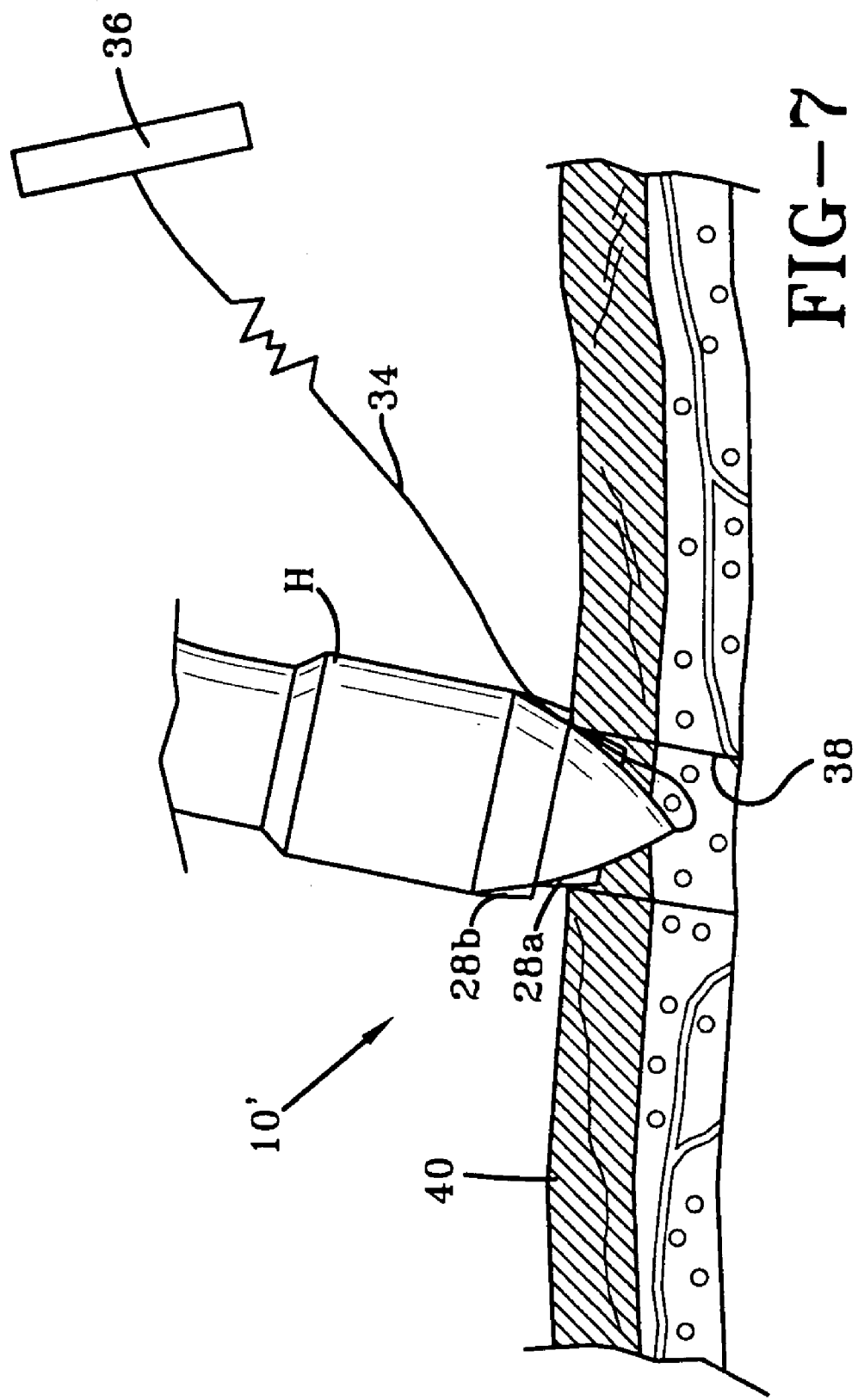
FIG. 7 shows the initial insertion of a stapler head having the introducer device of this invention thereon, the device being introduced through an abdominal wall opening.

In FIG. 7, introducer device 10' is shown flush with head H, and being introduced through a hole 38 in an abdominal wall 40. Blades 28a, 28b aid in the insertion by separating the tissue therefore decreasing the resistance to passage.

Figure 8:
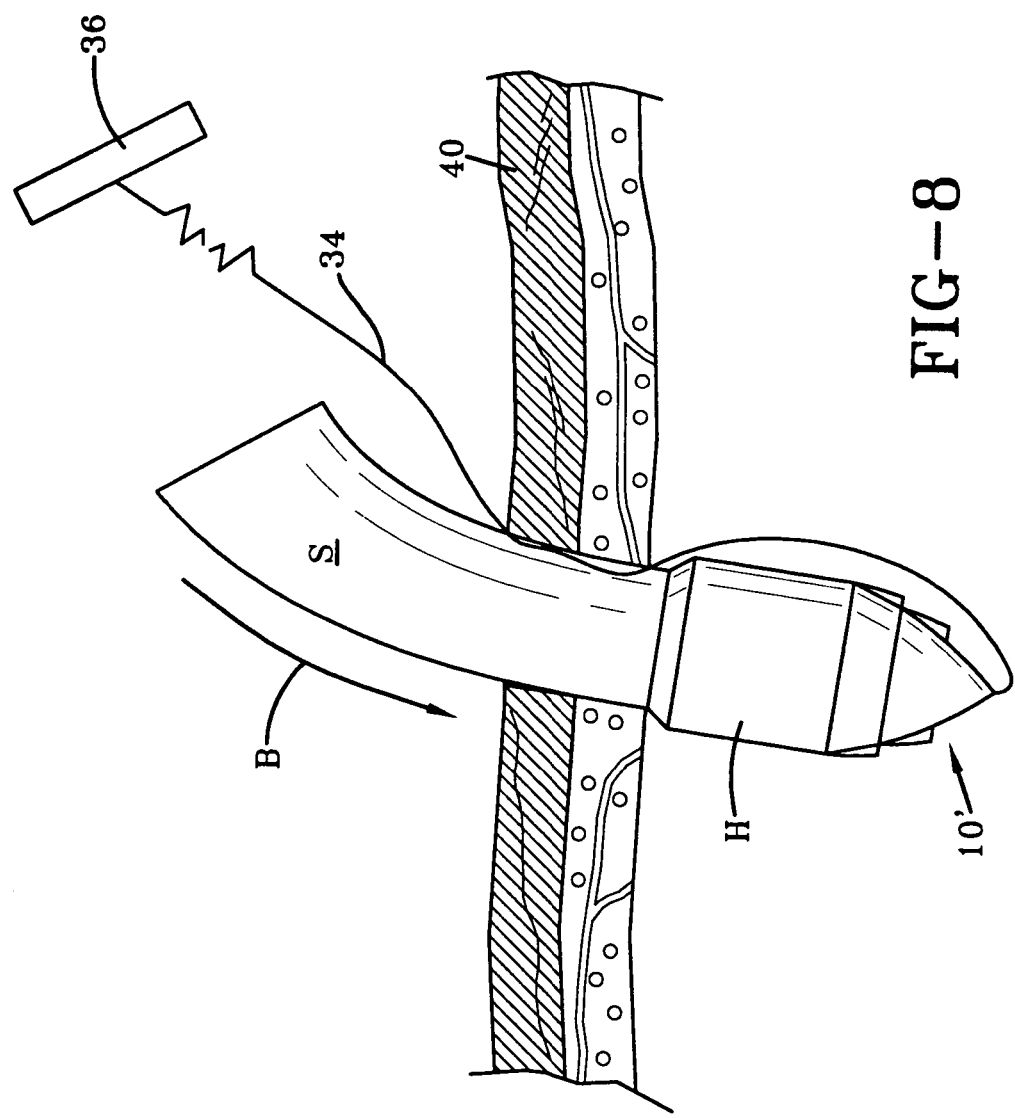
FIG. 8 shows the stapler and introducer device further inserted into the abdominal wall opening.
Figure 9:
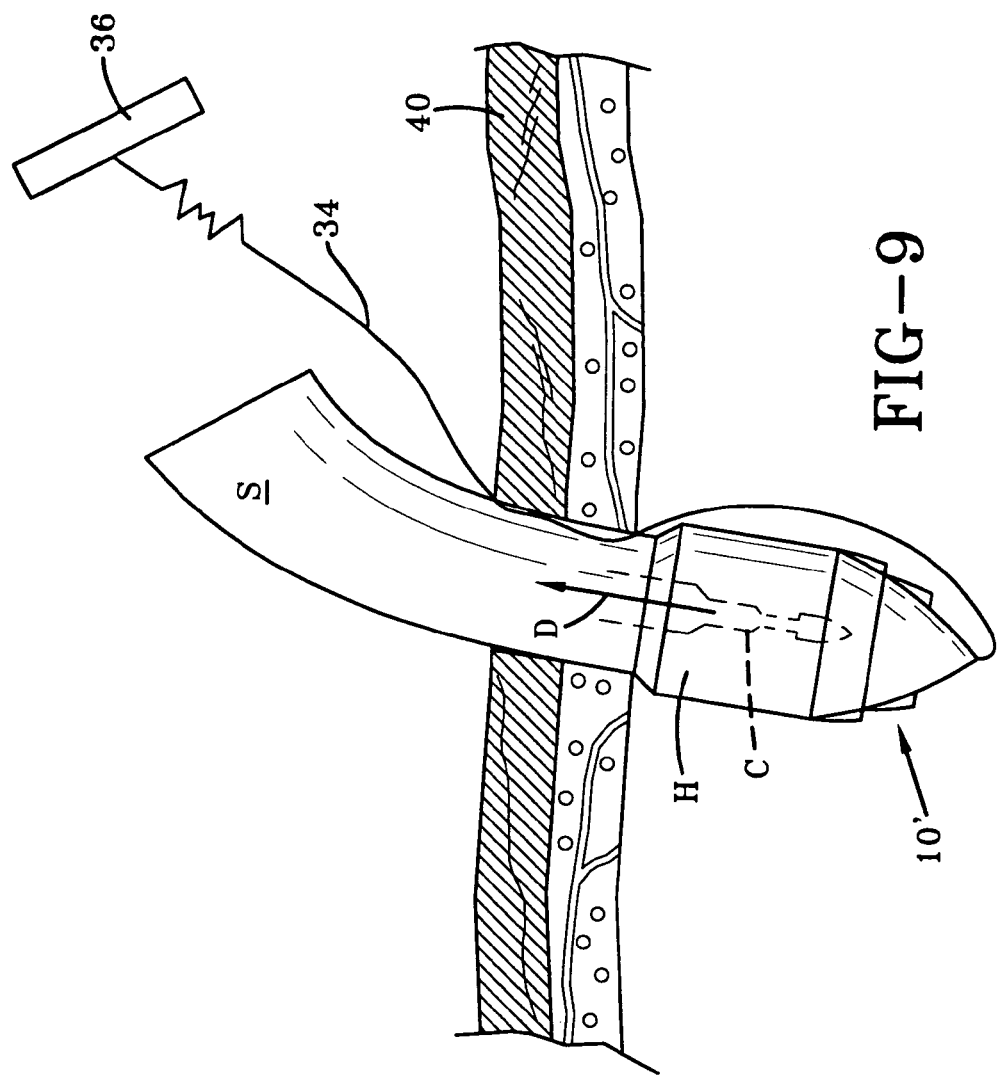
FIG. 9 shows the stapler and introducer device as in FIG. 8, with the center post being retracted to release the introducer device.
Figure 10:
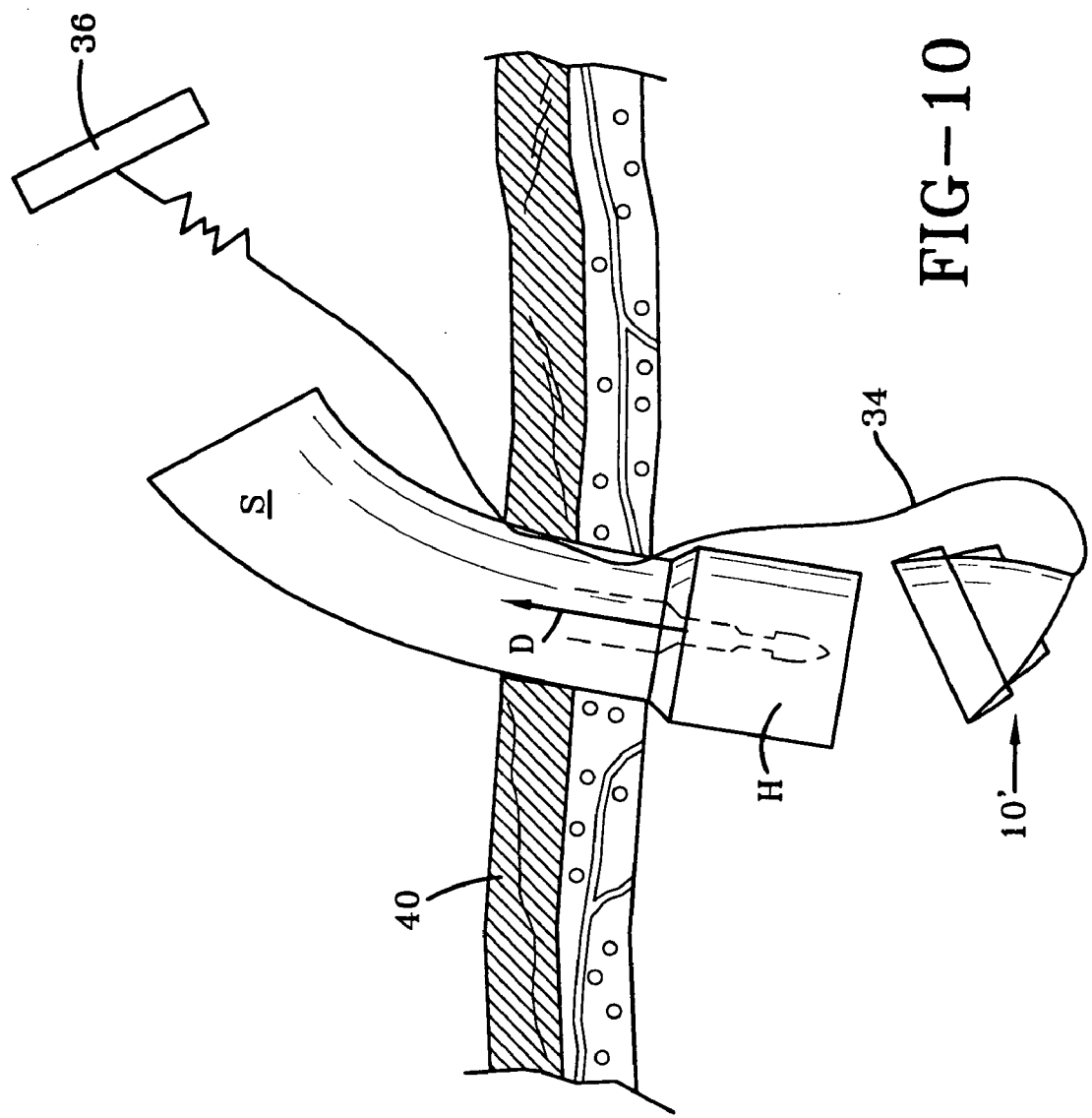
FIG. 10 shows the initial release of the introducer device from the stapler head.
Figure 11:
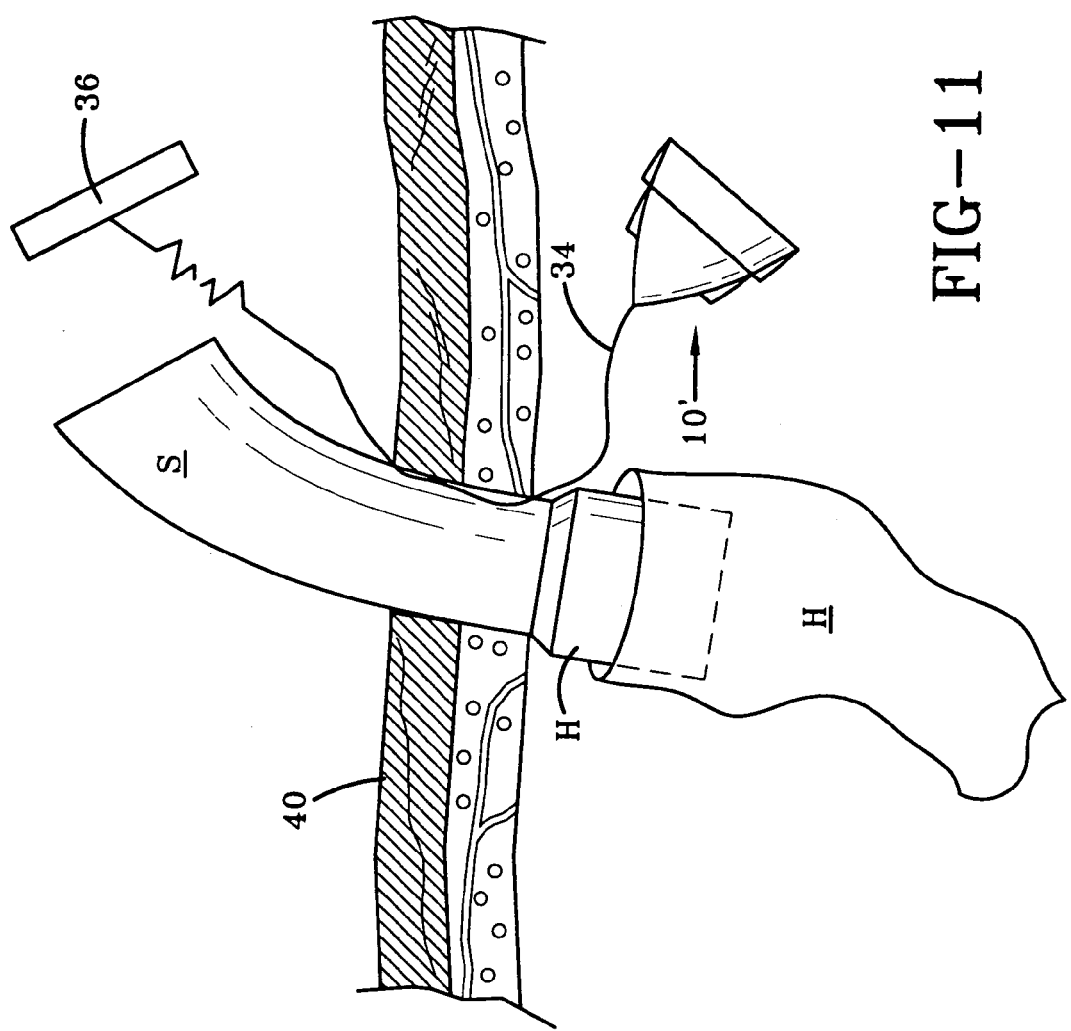
FIG. 11 shows the stapler head communicating with an intestine, and the introducer device being restricted from movement by a retraction wire.
Figure 12:
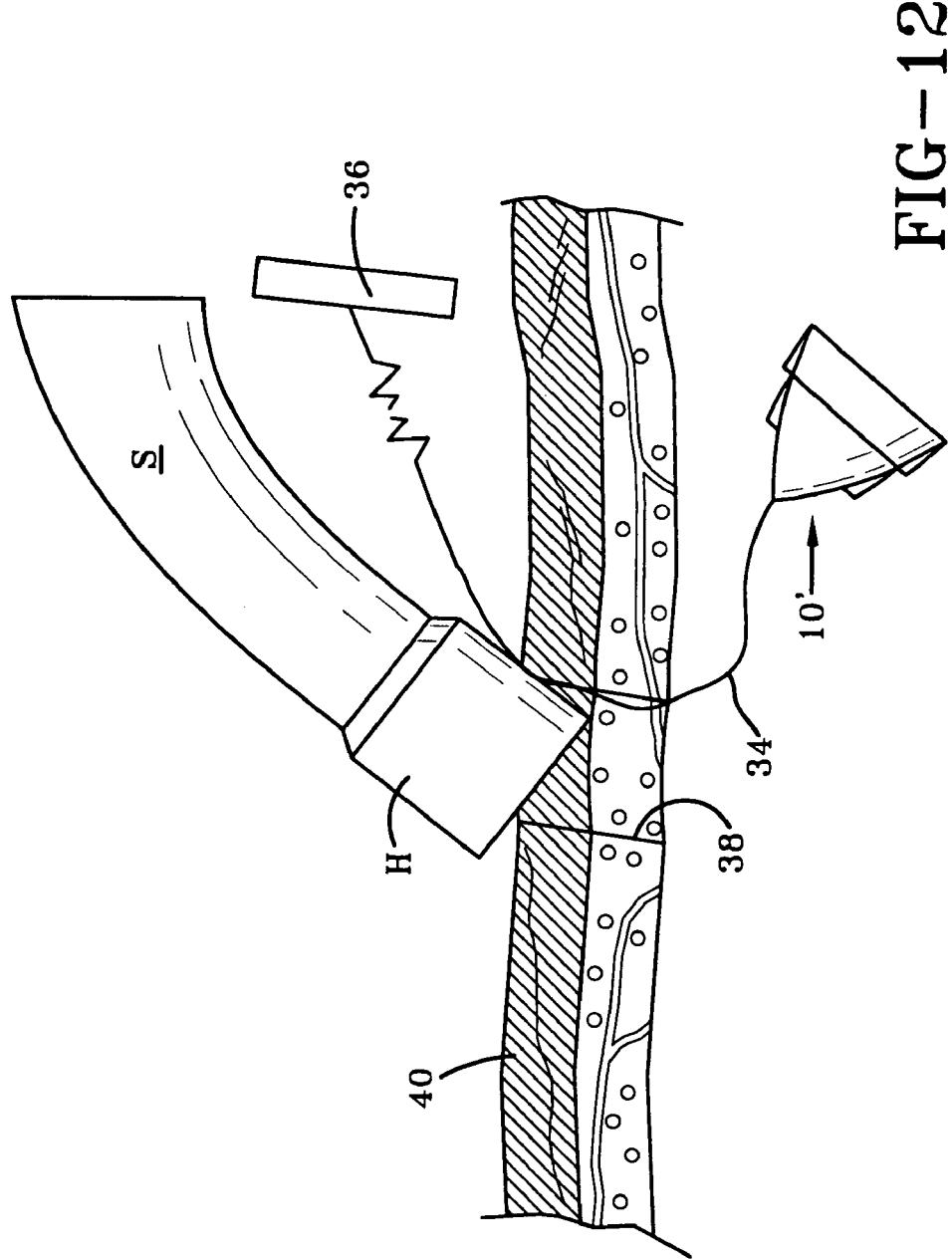
FIG. 12 shows the removal of the stapler head through the abdominal wall opening.

In FIG. 8, stapler S is further inserted in the direction of arrow B. In FIG. 9, having reached the desired positioning for head H, center rod C is retracted in the direction of arrow D, and the resiliency of rod bore 18a, at taper 20, allows for the detachment of center rod C from introducer device 10'. In FIG. 10, introducer device 10' is released from its flush joinder with head H. In FIG. 11, head H is inserted into an intestine I, by way of example, to show that a stapling operation may take place. Notably, introducer device 10' is retained by retraction wire 34. After performing the stapling operation, stapler S (stapler head H) is removed through hole 38, as in FIG. 12. Finally, as shown in FIG. 13, grip 36 may be pulled to remove introducer device 10' in a proper orientation, with the taper and blades in the lead.

In a particular embodiment, base end 16a of first body segment 14a has a diameter of 21 millimeters (mm), base end 16b of second body segment 14b has a diameter of 25 mm, base end 16c of third body segment 14c has a diameter of 29 mm, and base end 16d of fourth body segment 14d has a diameter of 33 mm. These dimensions are chosen to match existing stapler head insertion end diameters.

While a full and complete description of the invention has been set forth in accordance with the dictates of the patent statutes, it should be understood that modifications can be resorted to without departing from the spirit hereof or the scope of the this invention.

I claim:

1. An introducer device adapted for use with a plurality of surgical staplers, wherein each of the plurality of surgical staplers include a stapler head having an insertion end of circular cross section, a center rod having a tapered head and adapted to be selectively extendable beyond the insertion end of the stapler head and selectively retractable into the stapler head, each stapler head of each of the plurality of surgical staplers having a different diameter, the introducer device comprising:

(a) a first body segment including:
      an insertion end opposite a base end,
      a sidewall tapering from said base end to said insertion end to define an insertion tip,
      a center rod bore extending from an open end thereof at said base end toward said insertion tip and having a head grip portion adapted to selectively engage the tapered head of the center rod of any of the plurality of surgical staplers to secure said first body segment to cover said tapered head of said center rod, and
      a female connection bore extending from an open end thereof at said base end toward said insertion end; and (b) a second body segment including:
      an insertion end opposite a base end,
      a sidewall tapering from said base end to said insertion end,
      a through aperture adapted to received the center rod of any of the plurality of surgical staplers, and
      a male connection member extending from said insertion end to selectively engage said female connection bore of said first body segment, wherein said base end of said first body segment has a base end diameter substantially equal to the diameter of the insertion end of the stapler head of one of the plurality of surgical staplers and said base end of said second body segment has a base end diameter substantially equal to the diameter of the insertion end of the stapler head of another of the plurality of surgical staplers, said base end diameter of said first body segment being smaller than said base end diameter of said second body segment.

2. The introducer device of claim 1, wherein said insertion end of said second body segment has an insertion end diameter that is substantially equal to the base end diameter of said base end of said first body segment.

3. The introducer device of claim 2, further comprising:
   (c) a third body segment including:
      an insertion end opposite a base end,
      a sidewall tapering from said base end to said insertion end,
      a through aperture adapted to received the center rod of any of the plurality of surgical staplers, and
      a male connection member extending from said insertion end to selectively engage said female connection bore of said second body segment, wherein said second body segment has a base end diameter substantially equal to the diameter of said insertion end of said third body segment, and said third body segment has a base end diameter substantially equal to the diameter of the stapler head of another of the plurality of surgical staplers, said base end diameter of said second body segment being smaller than said base end diameter of said third body segment.

4. The introducer device of claim 3, further comprising:
   (c) a fourth body segment including:
      an insertion end opposite a base end,
      a sidewall tapering from said base end to said insertion end,
      a through aperture adapted to received the center rod of any of the plurality of surgical staplers, and
      a male connection member extending from said insertion end to selectively engage said female connection bore of said third body segment, wherein said third body segment has a base end diameter substantially equal to the diameter of said insertion end of said fourth body segment, and said fourth body segment has a base end diameter substantially equal to the diameter of the stapler head of another of the plurality of surgical staplers, said base end diameter of said third body segment being smaller than said base end diameter of said fourth body segment.

5. The introducer device of claim 1, further comprising blades extending from said first body segment.

6. The introducer device of claim 1, further comprising a retraction wire affixed proximate said insertion end of said first body segment.

* * * * *